United States Patent [19]

Linhares

[11] Patent Number: 5,336,218
[45] Date of Patent: Aug. 9, 1994

[54] SURGICAL SMOKE EVACUATOR SYNCHRONIZING SYSTEM

[75] Inventor: Stephen J. Linhares, Taunton, Mass.

[73] Assignee: Laser Engineering, Inc., Milford, Mass.

[21] Appl. No.: 77,120

[22] Filed: Jun. 15, 1993

[51] Int. Cl.⁵ .............................................. A61B 17/36
[52] U.S. Cl. ........................................ 606/10; 604/26; 604/23; 128/747
[58] Field of Search .............................. 606/10, 11, 12; 604/23–28, 30, 35; 361/187, 195; 307/52; 324/522; 128/747

[56] References Cited

U.S. PATENT DOCUMENTS

| | | | |
|---|---|---|---|
| 3,270,800 | 9/1966 | Deziel et al. | 361/195 X |
| 4,715,372 | 12/1987 | Philippbar et al. | 606/10 X |
| 4,971,034 | 11/1990 | Doi et al. | 606/10 X |
| 5,008,777 | 4/1991 | Yoshida et al. | 361/187 |
| 5,098,375 | 3/1992 | Baier | 604/26 X |
| 5,108,389 | 4/1992 | Cosmescu | 606/10 |
| 5,140,984 | 8/1992 | Dew et al. | 606/11 X |
| 5,199,944 | 4/1993 | Cosmescu | 606/10 X |

*Primary Examiner*—Peter A. Aschenbrenner
*Attorney, Agent, or Firm*—Joseph S. Iandiorio; Kirk Teska

[57] ABSTRACT

A surgical smoke evacuator synchronizing system includes a smoke evacuator system; a smoke or debris generating surgical device having a power cord with a plug for connection to a power source; and a monitoring system including a first receptacle for receiving the plug of the power cord; a cable connected to the first receptacle having a number of lines and having a second plug for connection to a power source receptacle; a current sensing loop for receiving at least one line of the cable; a detector circuit for sensing the current level in the cable; and a control device, responsive to a level of current in the cable, representing that the surgical device is operating, for enabling the smoke evacuator system and responsive to a level of current in the cable representing that the surgical device has completed operating for disabling the smoke evacuator system.

4 Claims, 4 Drawing Sheets

SURGICAL SMOKE EVACUATOR SYNCHRONIZING SYSTEM

FIELD OF INVENTION

This invention relates to a surgical smoke evacuator synchronizing system for coordinating operation of surgical devices which generate smoke and debris with available smoke evacuators.

BACKGROUND OF INVENTION

In certain surgical procedures such as those using laser and electrocautery devices, smoke and debris are generated from the ablating or burning of tissue. The smoke and debris obscures vision, smells bad, causes contamination and fouling of the surgical and other equipment, and creates smoke and particulate matter which may be breathed by the surgical personnel, an important and discomforting problem in view of the present concerns over the effects of inhaling particulate matter and over contracting AIDS. For these reasons smoke evacuators are used in surgical theaters where fouled air may be generated but they have a number of shortcomings. They are basically vacuum cleaners and so are generally noisy enough to distract or annoy personnel and even drown out conversation and commands. One solution to this problem has been to provide a foot switch which the surgeon can actuate on an as-needed basis. This approach is not all that convenient as in modern operating rooms surgeons are already faced with a number of foot switch actuated devices including the laser or electrocautery device, for example. Another approach is to integrate a smoke evacuator with each smoke or debris generating device, but this is needlessly redundant and adds the further expense and complexity of the electronic logic circuits required to synchronize the operation of the smoke or debris generated instrument and the smoke evacuator.

SUMMARY OF THE INVENTION

It is therefore an object of this invention to provide an improved surgical smoke evacuator actuating system.

It is a further object of this invention to provide such a surgical smoke evacuator actuating system which is simple, reliable and does not require foot switch actuation or any other specific actuation by surgical personnel.

It is a further object of this invention to provide such a surgical smoke evacuator actuating system which operates a smoke evacuator automatically, synchronously with operation of the smoke or debris generating surgical instrument.

It is a further object of this invention to provide such a surgical smoke evacuator which is not limited to use with a single surgical instrument or class of surgical instruments.

The invention results from the realization that a truly automatic and universally compatible system for synchronizing operation of smoke and debris generating surgical devices and smoke evacuators can be achieved using a monitoring unit which receives the power line from the surgical device, monitors the current in the power line to detect when the surgical device is on and off, and automatically operates the smoke evacuator accordingly.

This invention features a surgical smoke evacuator synchronizing system having a smoke evacuator system and a smoke or debris generating surgical device having a power cord with a plug for connection to a power source. A monitoring system includes a first receptacle for receiving the plug of the power cord, a cable connected to the first receptacle and having a number of lines, and a second plug for connection to a power source receptacle. The current sensing loop receives at least one line of the cable. A detector circuit senses the current level in the cable. There are control means responsive to a level of current in the cable representing that the surgical device is operating for enabling the smoke evacuator system and responsive to a level of current in the cable representing that the surgical device has completed operating for disabling the smoke evacuator system. The control means may include a control circuit and an actuator circuit in the smoke evacuator system. The actuator circuit may control power to the smoke evacuator system and the control circuit may operate the actuator circuit. Alternatively, the control means may directly control the power to energize the smoke evacuator system. The control means may also include delay means for disabling the smoke evacuator system a predetermined time after the surgical device has ceased operating.

DISCLOSURE OF PREFERRED EMBODIMENT

Other objects, features and advantages will occur to those skilled in the art from the following description of a preferred embodiment and the accompanying drawings, in which.

The surgical smoke evacuator synchronizing system according to this invention may be accomplished using a smoke evacuator system such as a BI-PURE 1000 smoke evacuator available froth Laser Engineering, Inc., of Milford, Mass., or a similar device, in conjunction with a smoke- or debris-generating surgical device having a power cord with a plug for connection with a power source. Such a surgical device may be a surgical laser such as an Access 40, 60, 80 or 100, or an MD 30, 40, 50, or 75, available from Laser Engineering, Inc., of Milford, Mass.; an electrocautery device; or any similar device which ablates, vaporizes, burns, or otherwise creates smoke and/or debris during surgical procedures. A monitoring system is used to interface between the smoke evacuator system and the surgical device. The monitoring system includes a first receptacle for receiving the plug of the power cord from the surgical device, a multi-line cable which is connected to that first receptacle, and a second plug for connection to a power source receptacle such as a wall receptacle. The monitoring system includes a current sensing loop which receives at least one line of the cable. A detector senses the current level in the cable and a control means is responsive to a level of current in the cable representing that the surgical device is operating for enabling the smoke evacuator system and responsive to the level of current in the cable representing that the surgical device has completed operating, for disabling the smoke evacuator system. The control means may include a control circuit in the monitoring system such as a relay or semiconductor switching circuit, which closes a circuit that connects a low-voltage, for example 24 volt, power supply to a relay in the actuator circuit in the smoke evacuator. That relay, which also may be a semiconductor switching circuit, closes the circuit including the power lines of the smoke evacuator, to energize the motor that drives the vacuum device. Alternatively, the actuator circuit, such as a relay or semiconductor switching device in the smoke evacuator, can be eliminated, and the AC power delivered to the smoke evacuator may be switched through the relay or semiconductor switching circuit in the control circuit in the monitoring system in order to energize the vacuum motor in the smoke evacuator. In yet another approach, the control circuit in the monitoring system can close the AC power circuit to the vacuum motor in the smoke evacuator by applying the power available at the monitoring system rather than switching the power supply to a separate line at the evacuator.

Figure 1:
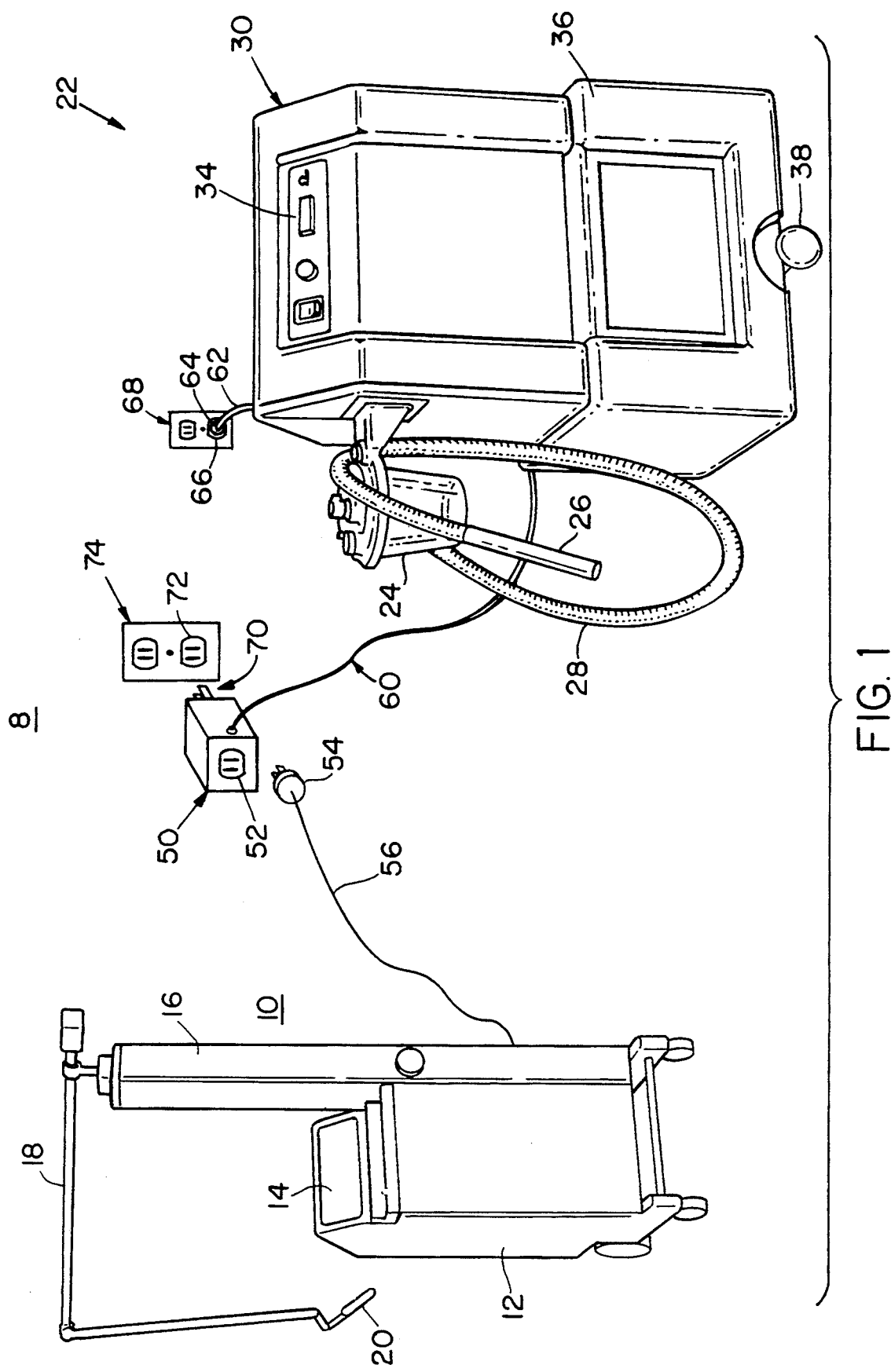
FIG. 1 is a three-dimensional view of a surgical smoke evacuator synchronizing system according to this invention.

There is shown in FIG. 1 a surgical smoke evacuator synchronizing system 8 according to this invention including a surgical laser system 10 having a power supply 12 and control panel 14 for operating $CO_2$ laser 16 whose output beam is directed through articulated arm 18 to a handpiece 20 which is directed by the surgeon to the portion of the patient to be addressed. A smoke evacuator 22 may include fluid canister 24, suction wand 26, and six feet of suction hose 28 or similar attachments. Housing 30 includes a control panel 34 including mode select switches, motor controllers, clocks, clock resets, and similar devices. Housing 30 also contains the evacuation components and the vacuum drive motor. The entire housing 30 may be mounted on a mobile dolly 36 having wheels 38, only one set of which is shown, so that the entire apparatus can be easily wheeled around the operating room for use with different pieces of equipment.

Interconnecting surgical laser 10 and smoke evacuator 22 is monitoring system 50, which includes a receptacle 52 for receiving plug 54 of power line cord 56, which energizes surgical laser 10. Control line 60 interconnects monitoring system 50 and smoke evacuator 22, whose own line cord 62 terminates in a plug 64 for engagement with receptacle 66 forming a part of a conventional wall receptacle 68. Monitoring system 50 has a plug 70 that is receivable in receptacle 72 which forms a part of wall receptacle 74.

Figure 2:
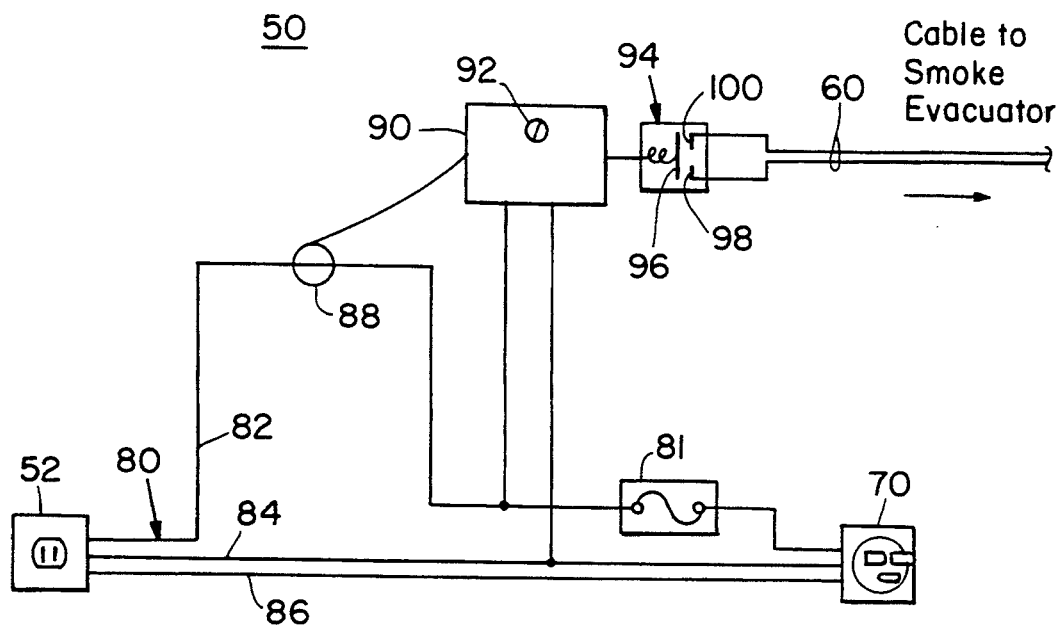
FIG. 2 is a schematic diagram of the monitoring system of FIG. 1.

Inside of monitoring system 50, FIG. 2, contacts of receptacle 52 are connected to three wire cable 80 having a hot wire 82, neutral wire 84, and ground wire 86. Current sensing loop 88 is installed on hot wire 82 which includes fuse 81. The output from current sensing loop 88 is delivered from current monitor circuit to a conventional current monitor circuit 90 which has an adjusting potentiometer so that the threshold level can be set as desired. When the threshold is reached, a control means such as relay 94 closes so that movable contact 96 shunts across and closes contacts 98 and 100.

Figure 3:
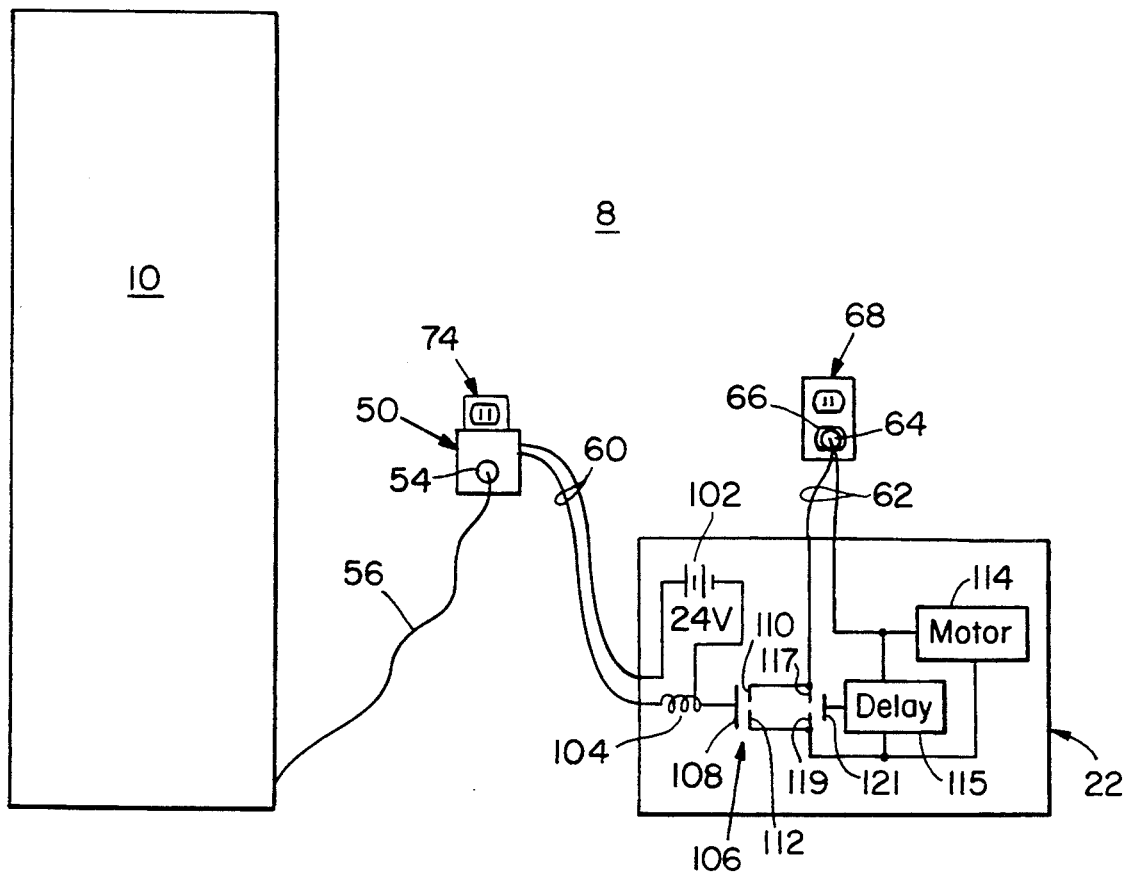
FIG. 3 is a schematic diagram similar to FIG. 1 showing the actuator circuit in the smoke evacuator operated by the control circuit in FIG. 2.

Control lines 60, FIG. 3, are connected in series with a low-voltage power supply such as 24-volt power supply 102 and relay coil 104 in smoke evacuator 22. Thus when relay 94, FIG. 2, is actuated, relay 106, FIG. 3, is caused to close so that contact 108 shunts across contacts 110 and 112, completing the connection of vacuum motor 114 to the 110-volt power supply over power cord 62 through plug 64 received in receptacle 66 of wall outlet 68.

Often to be sure that the smoke is thoroughly purged from the area it is desirable to continue the smoke evacuation for a short time after the surgical laser 10 has ceased operation. In that case a delay timer 115, FIG. 3, can simultaneously with motor 114 be actuated to close contacts 117, 119 with its contact 121. Then even when contact 108 opens contacts 110 and 112 power will keep flowing to motor 114 through contacts 117, 119, 121 until delay timer 115 finally times out and breaks the contact. The delay may be set for seconds or minutes or any duration as needed.

Figure 4:
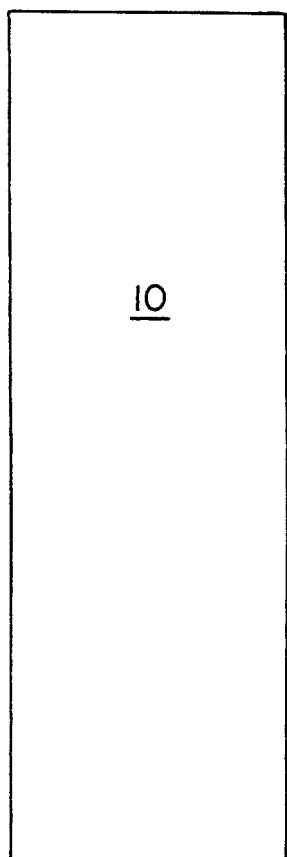
FIG. 4 is a view similar to FIG. 3 showing an alternative technique for operating the smoke evacuator.
Figure 4:
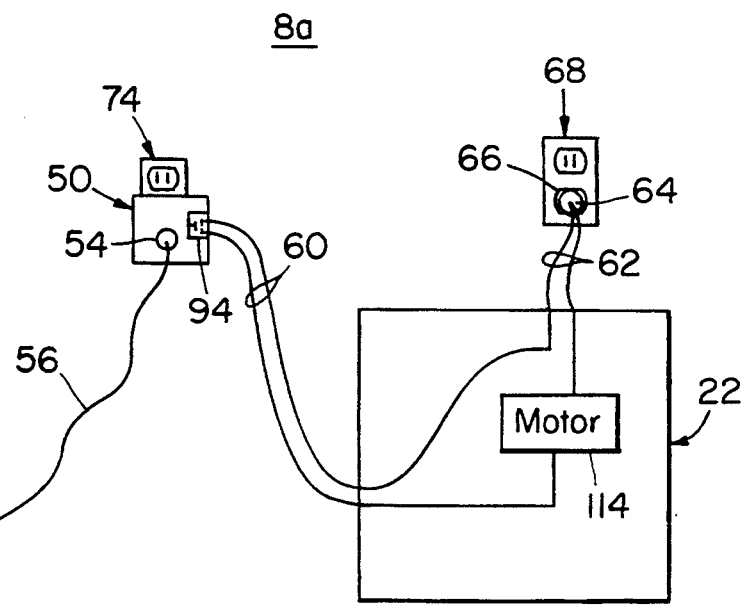

Alternatively, FIG. 4, the control means may include only relay 94, FIG. 2, and eliminate relay 106 in the smoke evacuator 22. In that case, FIG. 4, the power circuit, beginning at plug 64 and continuing through power line 62 to motor 114, is completed in the control circuit in monitoring system 50 which is constituted by relay 94. Thus the AC power to motor 114 is supplied without the intervening 24-volt control circuit in smoke evacuator 22 as shown in FIG. 3.

Figure 5:
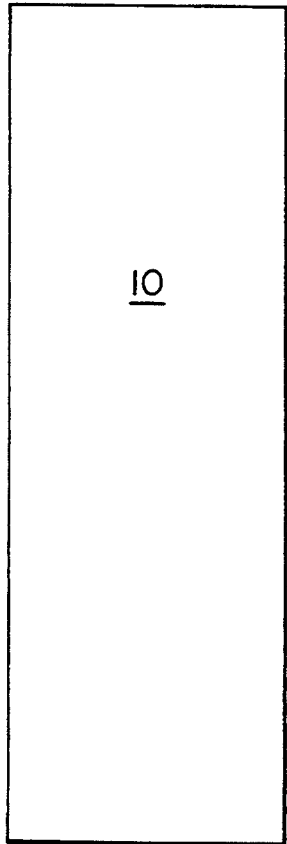
FIG. 5 is a view similar to FIG. 4 showing yet another way of actuating the smoke evacuator.
Figure 5:
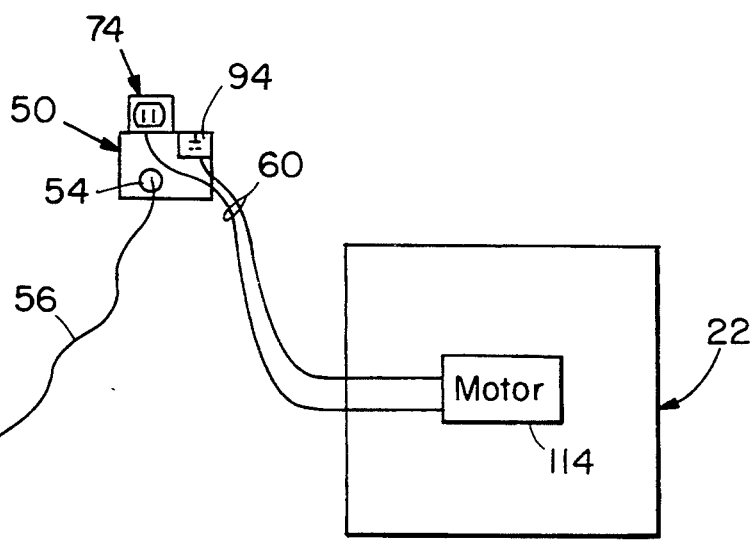
Figure 6:
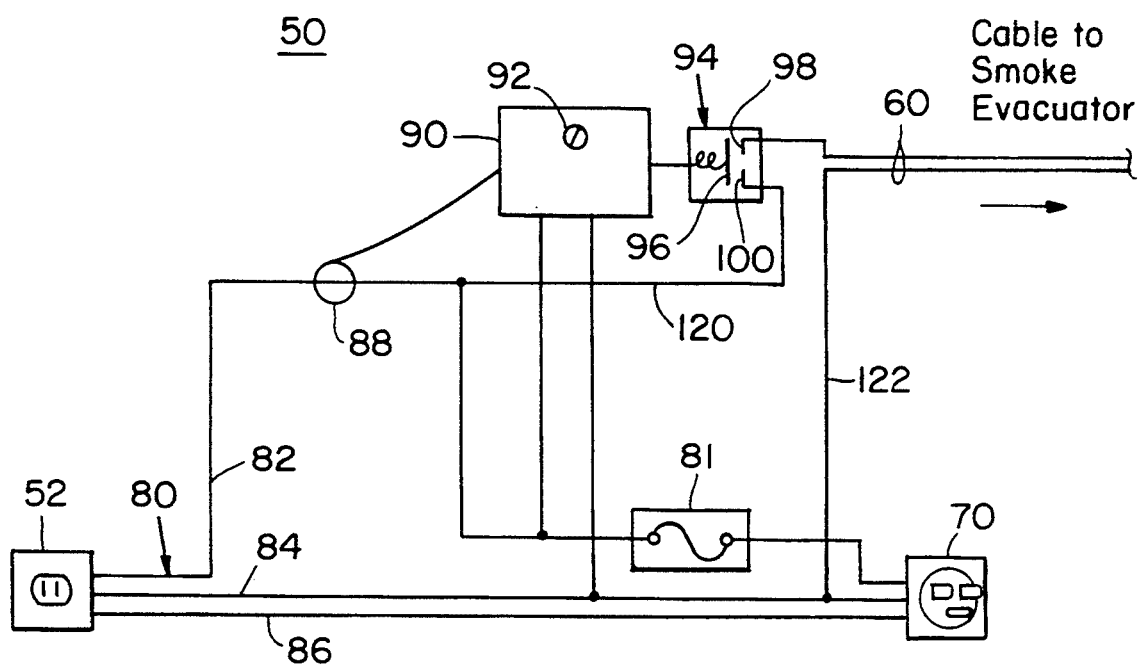
FIG. 6 is a schematic diagram similar to that of FIG. 2 modified to operate in the configuration as shown in FIG. 5.

In yet another construction, motor 114, FIG. 5, of smoke evacuator 22 may be powered completely through relay 94 in monitoring system 50. This is done by using relay 94 not just to close the circuit from the local AC power supply at smoke evacuator 22 to the smoke evacuator motor 114, but to actually apply the AC power available at monitoring system 50 through line 60 to motor 114. This can be more clearly seen in FIG. 6, where the AC available in cable 80 in monitoring system 50 is supplied directly from the hot line 82 over line 120 and the neutral line 84 over line 122, to cable 60 and relay 94 so that the control of the power to motor 114 not only occurs in monitoring system 50, but actually employs the AC power available in monitoring system 50 to energize motor 114. Although this disclosure may imply the system operates on 60 Hz 110 volt a.c. power, this is not a necessary limitation. Other frequencies, e.g., 50 Hz, and other voltages, e.g., 220, would work as well.

Although specific features of this invention are shown in some drawings and not others, this is for convenience only as some feature may be combined with any or all of the other features in accordance with the invention.

Other embodiments will occur to those skilled in the art and are within the following claims:

What is claimed is:

1. A surgical smoke evacuator synchronizing system, comprising:
   a smoke evacuator system;
   a smoke or debris generating surgical device having a power cord with a plug for connection to a power source;
   a monitoring system including a first receptacle for receiving said plug of said power cord; a cable connected to said first receptacle and having a number of lines and having a second plug for connection to a power source receptacle; a current sensing loop for receiving at least one line of said cable; a detector circuit for sensing the current level in said cable; and control means, responsive to a level of current in said cable, representing that said surgical device is operating, for enabling said smoke evacuator system and responsive to a level of current in said cable representing that said surgical device has completed operating for disabling said smoke evacuator system.

2. The surgical smoke evacuator synchronizing system of claim 1 in which said control means includes a control circuit in said monitoring system and an actuator circuit in said smoke evacuator system, said actuator circuit controls power to said smoke evacuator system and said control circuit operates said actuator circuit.

3. The surgical smoke evacuator synchronizing system of claim 1 in which said control means includes means for directly controlling the power to energize said smoke evacuator system.

4. The surgical smoke evacuator synchronizing system of claim 1 further including delay means for disabling said smoke evacuator system a predetermined time after said surgical device has completed operating.

* * * * *